(12) United States Patent
Hoshino et al.

(10) Patent No.: US 12,110,403 B2
(45) Date of Patent: *Oct. 8, 2024

(54) INKJET INK AND TABLET

(71) Applicant: TOPPAN PRINTING CO.,LTD., Tokyo (JP)

(72) Inventors: Yuichi Hoshino, Tokyo (JP); Masatoshi Saito, Tokyo (JP)

(73) Assignee: TOPPAN PRINTING CO., LTD., Tokyo (JP)

(*) Notice: Subject to any disclaimer, the term of this patent is extended or adjusted under 35 U.S.C. 154(b) by 917 days.

This patent is subject to a terminal disclaimer.

(21) Appl. No.: 17/029,607

(22) Filed: Sep. 23, 2020

(65) Prior Publication Data

US 2021/0002503 A1  Jan. 7, 2021

Related U.S. Application Data

(63) Continuation of application No. PCT/JP2019/014363, filed on Mar. 29, 2019.

(30) Foreign Application Priority Data

Mar. 29, 2018  (JP) ................................ 2018-065717

(51) Int. Cl.
  *C09D 11/322* (2014.01)
  *A61K 9/20* (2006.01)
  *C09D 11/38* (2014.01)

(52) U.S. Cl.
  CPC .......... *C09D 11/322* (2013.01); *A61K 9/2072* (2013.01); *C09D 11/38* (2013.01)

(58) Field of Classification Search
  CPC ..... C09D 11/322; C09D 11/38; C09D 11/328; A61K 9/2072
  See application file for complete search history.

(56) References Cited

U.S. PATENT DOCUMENTS

2005/0061184 A1   3/2005  Russell et al.

FOREIGN PATENT DOCUMENTS

CN    103275560 A      9/2013
EP         911372 A1 *  4/1999  ........... C09D 11/328
(Continued)

OTHER PUBLICATIONS

English machine translation of JP-2015003883-A (Year: 2015).*
(Continued)

*Primary Examiner* — Jennifer A Smith
*Assistant Examiner* — Jeffrey Eugene Barzach
(74) *Attorney, Agent, or Firm* — Foley & Lardner LLP (57) ABSTRACT

An inkjet ink in which a food color containing at least sodium copper chlorophyllin and a pigment other than sodium copper chlorophyllin is dispersed in a dispersion medium containing propylene glycol, and which prevents the occurrence of precipitation of the pigment components or other components even when the inkjet ink is stored for a long period of time, and there is also provided a tablet having a print pattern printed by the inkjet ink. The inkjet ink of the present embodiment, which is edible, comprises a food color containing at least sodium copper chlorophyllin and a pigment other than sodium copper chlorophyllin, and a dispersion medium containing propylene glycol, and has a propylene glycol content in the range of 0.001 mass % or more and 19 mass % or less relative to the total mass of the inkjet ink.

7 Claims, 3 Drawing Sheets

(56) References Cited

FOREIGN PATENT DOCUMENTS

| JP | 2000-191969 A | | 7/2000 | |
|----|---------------|---|--------|---|
| JP | 2004-155962 A | | 6/2004 | |
| JP | 2004-168880 A | | 6/2004 | |
| JP | 2006-169301 A | | 6/2006 | |
| JP | 2008-285519 A | | 11/2008 | |
| JP | 2010065149 A | * | 3/2010 | |
| JP | 2015003883 A | * | 1/2015 | ........... A61K 9/2072 |
| JP | 2015-218268 A | | 12/2015 | |
| KR | 20110069469 A | * | 6/2011 | |
| WO | WO-0194116 A2 | * | 12/2001 | ........... A23G 3/0097 |
| WO | WO-2016/117518 A1 | | 7/2016 | |

OTHER PUBLICATIONS

English machine translation of JP-2010065149-A (Year: 2010).*
English machine translation of KR-20110069469-A (Year: 2011).*
Extended European Search Report dated Apr. 14, 2021 for corresponding European Patent Application No. 19775483.1.
Office Action issued on Mar. 23, 2021 for corresponding Japanese Patent Application No. 2020-509371.
International Searching Authority, "International Search Report," issued in connection with International Patent Application No. PCT/JP2019/014363, dated Jun. 25, 2019.
International Searching Authority, "Written Opinion," issued in connection with International Patent Application No. PCT/JP2019/014363, dated Jun. 25, 2019.

* cited by examiner

INKJET INK AND TABLET

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2019/014363, filed on Mar. 29, 2019, which is based upon and claims the benefit of priority to Japanese Patent Application No. 2018-065717, filed on Mar. 29, 2018, the disclosures of which are all incorporated herein by reference in their entireties.

BACKGROUND

Technical Field

The present invention relates to an inkjet ink and a tablet.

Background Art

Inkjet printing inks (which may be simply termed inkjet ink(s) hereinafter) include those inks which are edible. A technique related to an edible inkjet ink is disclosed, for example, in PTL 1.

For example, some edible inkjet inks that are available are obtained by dispersing a food color in a dispersion medium containing propylene glycol. The food color in this case comprises at least sodium copper chlorophyllin (chlorophyllin copper complex sodium, CAS Number: 28302-36-5) and a pigment other than sodium copper chlorophyllin.

[Citation List] [Patent Literature] [PTL 1] JP 2006-169301 A

SUMMARY OF THE INVENTION

Technical Problem

If an inkjet ink comprising the above sodium copper chlorophyllin is stored for a long period of time, e.g., one year or more, the pigment components or other components may be precipitated and the precipitation may impair resumability of printing.

The present invention has been made in light of the circumstances set forth above and aims to provide an inkjet ink in which a food color containing at least sodium copper chlorophyllin and a pigment other than sodium copper chlorophyllin is dispersed in a dispersion medium containing propylene glycol, and which prevents the occurrence of precipitation of the pigment components or other components even when the inkjet ink is stored for a long period of time, and a tablet provided with a print pattern printed by the inkjet ink.

Solution to Problem

An inkjet ink according to an aspect of the present invention is edible and comprises a food color containing at least sodium copper chlorophyllin and a pigment other than the sodium copper chlorophyllin, and a dispersion medium containing propylene glycol. In the inkjet ink, a content of the propylene glycol is in a range of 0.001 mass % or more and 19 mass % or less relative to a total mass of the inkjet ink.

Advantageous Effects of the Invention

According to the aspect of the present invention, even after long-term storage of an inkjet ink in which a food color containing at least sodium copper chlorophyllin and a pigment other than sodium copper chlorophyllin is dispersed in a dispersion medium containing propylene glycol, the pigment components or other components can be prevented from being precipitated and printing can be easily resumed compared to the conventional art.

DETAILED DESCRIPTION

Embodiments of the present invention will be described below with reference to the drawings. In the following description of the drawings to be referred, components identical with or similar to each other are given the same or similar reference signs. It should be noted that the drawings are only schematically illustrated, and thus the relationship between thickness and two-dimensional size of the components, and the thickness ratio between the layers, are not to scale. Therefore, specific thicknesses and dimensions should be understood in view of the following description. As a matter of course, dimensional relationships or ratios may be different between the drawings.

Further, the embodiments described below are merely examples of configurations for embodying the technical idea of the present invention. The technical idea of the present invention does not limit the materials, shapes, structures, arrangements, and the like of the components to those described below. The technical idea of the present invention can be modified variously within the technical scope defined by the claims.

An inkjet ink according to an embodiment of the present invention is an inkjet ink which is used, for example, for printing characters, an image, or the like on a surface of a pharmaceutical tablet by inkjet printing. The following description specifically explains an inkjet ink according to an embodiment of the present invention and a tablet having a print pattern printed by the inkjet ink.

[Composition of Inkjet Ink]

The inkjet ink of the present embodiment comprises at least a food color and a dispersion medium in which the food color can be dispersed. The food color of the present embodiment contains at least sodium copper chlorophyllin and a pigment other than sodium copper chlorophyllin. The dispersion medium of the present embodiment contains at least propylene glycol. The dispersion medium of the present embodiment has a propylene glycol content in the range of 0.001 mass % or more and 19 mass % or less relative to the total mass of the inkjet ink. An inkjet ink with this composition can prevent the pigment components or other components from being precipitated and enables easy resumption of printing even after a long-term storage of the inkjet ink. It should be noted that if the propylene glycol content is less than 0.001 mass % relative to the total mass of the inkjet ink, the inkjet ink may dry and impair resumability of printing. If the propylene glycol content exceeds 19 mass % relative to the total mass of the inkjet ink, the pigment components or other components may be precipitated and the precipitation may impair resumability of printing.

Advantageous effects achieved by the inkjet ink of the present embodiment will be described.

In the technical field of the inkjet ink of the present embodiment, if printability is adversely affected by sediments formed by aggregation of the pigment components or the like contained in the ink or by the impurities contained in the ink, production of the sediments or the impurities has been minimized by using a method of purifying the pigment components or the like contained in the ink or a method of adding a nitrite salt to the ink.

In this regard, the inkjet ink of the present embodiment prevents the occurrence of such precipitation and enables easy resumption of printing by controlling the content of propylene glycol as a dispersion medium in the ink. More specifically, for example, the inventor has found that the sediments due to sodium copper chlorophyllin added to the ink are less likely to be soluble in propylene glycol but are soluble in glycerin or water by a predetermined amount. Thus, the inventor controlled the content of propylene glycol in the ink and could prevent the occurrence of precipitation of the pigment components or other components and enabled easy resumption of printing even after long-term storage of the inkjet ink.

The inkjet ink of the present embodiment may have a propylene glycol content in the range of 0.01 mass % or more and 2.5 mass % or less relative to the total mass of the inkjet ink. With this composition, the pigment components or other components can be reliably prevented from being precipitated and easy resumption of printing can be reliably ensured, even when the inkjet ink is stored for a long period of time.

The inkjet ink of the present embodiment may have a food color content in the range of 1 mass % or more and 10 mass % or less relative to the total mass of the inkjet ink. With this composition, the pigment components or other components can be further prevented from being precipitated and easy resumption of printing can be better ensured, even when the inkjet ink is stored for a long period of time. If the food color content is less than 1 mass % relative to the total mass of the inkjet ink, readability (visibility) of the printed characters or the like may be impaired, and light resistance may also be impaired. If the food color content exceeds 10 mass % relative to the total mass of the inkjet ink, the pigment components or other components may be precipitated, impairing resumability of printing.

The inkjet ink of the present embodiment may comprise at least one of New Coccine, erythrosine and Brilliant Blue FCF, as a pigment other than sodium copper chlorophyllin. Sodium copper chlorophyllin is a green food color, while New Coccine is a red food color, which is referred to as Food Red No. 102 (Color Index name: Acid Red 18, CAS Number: 2611-82-7). Erythrosine is a red food color, which is referred to as Food Red No. 3 (FDA name: FD & C Red No. 3, Color Index name: Acid Red 51, CAS Number: 16423-68-0). Brilliant Blue FCF is a blue food color, which is referred to as Food Blue No. 1 (FDA name: FD & C Blue No. 1, Color Index name: Food Blue 2, CAS Number: 3844-45-9). With this composition, the inkjet ink can have a gray hue. The inkjet ink of the present embodiment may comprise tartrazine as a pigment other than sodium copper chlorophyllin. Tartrazine is a yellow food color, which is referred to as Food Yellow No. 4 (FDA name: FD & C Yellow No. 5, Color Index name: Acid Yellow 23, CAS Number: 1934-21-0). With this composition, the inkjet ink can have a yellow-green hue.

With the composition described above, the pigment components or other components can be further prevented from being precipitated and easy resumption of printing can be better ensured, even when the inkjet ink is stored for a long period of time.

The Color Index name mentioned above is defined by the American Association of Textile Chemists and Colorists. The FDA name mentioned above is defined by the Food and Drug Administration of the United States. Pigments (materials) that can be used in the present embodiment are specified by CAS Numbers, but the present invention is not limited to these. As a matter of course, for example, pigments that can be used in the present embodiment include those pigments which have the same names as those of the pigments (materials) mentioned in the present embodiment but have different CAS Numbers because of being geometric isomers, stereoisomers, materials comprising isotopes, or salts thereof. If there are no isomers or the like, or if pigments (materials) that can be used are specified (limited), the materials (compounds) having the CAS Numbers indicated in the present embodiment can be used.

The food color of the inkjet ink of the present embodiment may have a content of a pigment other than sodium copper chlorophyllin in the range of 0.1 parts by mass or more and 1.5 parts by mass or less relative to 1 part by mass of sodium copper chlorophyllin. With this composition, the pigment components or other components can be further prevented from being precipitated and easy resumption of printing can be better ensured, even when the inkjet ink is stored for a long period of time. If the food color contains less than 0.1 parts by mass of pigment other than sodium copper chlorophyllin relative to 1 part by mass of sodium copper chlorophyllin, the print pattern may have a high chroma level, with discoloration thereof after light exposure appearing to be pronounced, and accordingly may be recognized as having low light resistance. If the food color contains a pigment of more than 1.5 parts by mass other than sodium copper chlorophyllin relative to 1 part by mass of sodium copper chlorophyllin, the pigment components may be precipitated, impairing resumability of printing.

The inkjet ink of the present embodiment may further comprise glycerin as a dispersion medium, and the propylene glycol content may be less than the glycerin content. With this composition, drying speed at the nozzle of the inkjet head during printing may be reduced and easy resumption of printing is better ensured.

(Pigment)

As described above, the food color contained in the inkjet ink of the present embodiment necessarily comprises sodium copper chlorophyllin and a pigment other than sodium copper chlorophyllin. However, any pigments, as long as they are edible, may be used other than these two types of pigments. Pigments added to the inkjet ink of the present embodiment can be appropriately selected from, for example, known synthetic and natural food colors.

The synthetic food colors may include, for example, tar-based pigments, natural pigment derivatives, natural system synthetic pigments, and the like. Examples of the tar-based pigments include Food Red No. 2 (Amaranth, FDA name: FD & C Red No. 2, Color Index name: Acid Red 27, CAS Number: 915-67-3), Food Red No. 40 (Allura Red AC, FDA name: FD & C Red No. 40, Color Index name: Food Red 17, CAS Number: 25956-17-6), Food Red No. 102 (New Coccine, Color Index name: Acid Red 18, CAS Number: 2611-82-7), Food Red No. 104 (Phloxine, FDA name: FD & C Red No. 28, Color Index name: Acid Red 92, CAS Number: 18472-87-7), Food Red No. 105 (Rose Bengal, Color Index name: Acid Red 94, CAS Number: 632-69-9), Food Red No. 106 (Acid Red, Color Index name: Acid Red 52, CAS Number: 3520-42-1), Food Red No. 4 (Tartrazine, FDA name: FD & C Yellow No. 5, Color Index name: Acid Yellow 23, CAS Number: 1934-21-0), Food Yellow No. 5 (Sunset Yellow FCF, FDA name: FD & C Yellow No. 6, Color Index name: Food Yellow 3, CAS Number: 2783-94-0), Food Blue No. 1 (Brilliant Blue FCF, FDA name: FD & C Blue No. 1, Color Index name: Food Blue 2, CAS Number: 3844-45-9), Food Blue No. 2 (Indigo Carmine, FDA name: FD & C Blue No. 2, Color Index name: Acid Blue 74, CAS Number: 860-22-0), Food Red No. 2 aluminum lake (FD & C Red No. 2 Aluminum Lake), Food Red No. 3 aluminum lake (FD & C Red No. 3 Aluminum Lake), Food Red No. 40 aluminum lake (FD & C Red No. 40 Aluminum Lake), Food Yellow No. 4 aluminum lake (FD & C Yellow No. 5 Aluminum Lake), Food Yellow No. 5 aluminum lake (FD & C Yellow No. 6 Aluminum Lake), Food Blue No. 1 aluminum lake (FD & C Blue No. 1 Aluminum Lake), Food Blue No. 2 aluminum lake (FD & C Blue No. 2 Aluminum Lake), and the like. The natural pigment derivatives include, for example, norbixin potassium, and the like. The natural system synthetic pigments include, for example, ß-carotene, riboflavin, and the like.

Furthermore, examples of the natural food colors include anthocyanin pigments, carotenoid pigments, quinone pigments, flavonoid pigments, betaine pigments, Monascus pigments, and other pigments originating from natural products. Examples of anthocyanin pigments include red radish pigment, red cabbage pigment, red rice pigment, elderberry pigment, cowberry pigment, gooseberry pigment, cranberry pigment, salmon berry pigment, perilla pigment, sim blueberry pigment, strawberry pigment, dark sweet cherry pigment, cherry pigment, hibiscus pigment, huckleberry pigment, grape juice pigment, grape skin pigment, black currant pigment, blackberry pigment, blueberry pigment, plum pigment, whortleberry pigment, boysenberry pigment, mulberry pigment, purple yam pigment, purple corn pigment, Chinese purple yam pigment, raspberry pigment, red currant pigment, loganberry pigment, and other anthocyanin pigments. Examples of carotenoid pigments include annatto pigment, gardenia yellow pigment, and other carotenoid pigments. Examples of quinone pigments include cochineal pigment, lithospermum root pigment, lac pigment, and other quinone pigments. Examples of flavonoid pigments include safflower yellow pigment, kaoliang pigment, onion pigment, and other flavonoid pigments. Examples of betaine pigments include beet red pigment. Examples of the Monascus pigments include Monascus purpureus pigment, and Monascus yellow pigment. Examples of other pigments originating from natural products include turmeric pigment, Trichotomine pigment, gardenia red pigment, and spirulina blue pigment.

The hue of the inkjet ink can be controlled by the combination of the above pigments or by the combination of the contents of the pigments. For example, if the hue of the inkjet ink is desired to be gray, a green pigment of sodium copper chlorophyllin, a red pigment of New Coccine (Food Red No. 102) or erythrosine (Food Red No. 3), and a blue pigment of Brilliant Blue FCF (Food Blue No. 1) may be selected as food colors. Also, if the hue of the inkjet ink is desired to be yellow-green, a green pigment of sodium copper chlorophyllin, and a yellow pigment of tartrazine (Food Yellow No. 4) may be selected as food colors.

(Dispersion Medium)

The inkjet ink of the present embodiment may comprise a dispersion medium other than the above pigments to disperse the pigments therein. Examples of the dispersion medium that can be added to the inkjet ink of the present embodiment include purified water, ethanol, glycerin, propylene glycol, polyethyleneglycol 300 (having an average molecular weight of 300), 1-propanol, 2-propanol, and ethyl lactate. The mixing ratio of the medium is not particularly limited. It is more preferred, however, that the inkjet ink may have a content of any of glycerin, propylene glycol and polyethyleneglycol 300 in the range of 1 mass % or more and 30 mass % or less to prevent the ink from drying at the nozzle. If the content of the medium is less than 1 mass %, the ink may easily dry and cause clogging. If the content exceeds 30 mass %, an excessively long time may be taken for the printed surfaces of the pharmaceutical tablets to dry, and when these tablets are brought into contact with each other, undried ink of one tablet may adhere to another tablet and smear.

Pharmaceutical tablets are not particularly limited in the present embodiment. However, pronounced effects may be exerted when the inkjet ink is used for those tablets whose surfaces are covered with film coatings. This is considered to be because, when a print pattern is formed on the surface of a tablet, the pigment components easily remain on the surface, if the tablet is film-coated, due to having fewer voids than does an uncoated tablet, and thus because, when the printed surface is affected by light or moisture from outside, the effect of the light or moisture on the pigments is stronger for the film-coated tablet than for an uncoated tablet. Since an uncoated tablet has many voids, pigments may continue to penetrate therein over time, causing discoloration on the printed surface, and the discoloration may relatively reduce the effect of light or moisture.

(Internal-Sizing Resin)

The inkjet ink of the present embodiment may contain an internal-sizing resin other than the above pigments or dispersion medium. The internal-sizing resin that can be added to the inkjet ink of the present embodiment may be an edible resin-like material in the form of a water-soluble powder, paste or flakes which are capable of forming a coating on the surface of a tablet when dried after printing. Examples of the internal-sizing resin include polyvinyl alcohol (PVA), hydroxypropyl cellulose (HPC), hydroxypropyl methylcellulose (HPMC), polyvinylpyrrolidone (PVP), high molecular weight polyethylene glycol (PEG) such as polyethylene glycol 4000 or polyethylene glycol 1540, shellac resin, methacrylic acid copolymer (product name: Eudragit S100), maltodextrin, erythritol, and the like.

(Leveling Agent)

The inkjet ink of the present embodiment may contain a leveling agent other than the above pigments, dispersion medium or internal-sizing resin. The levelling agent that can be added to the inkjet ink of the present embodiment may be an edible and water-soluble surfactant. Examples of the levelling agent include polyglycerin fatty acid ester (e.g., Decaglyceryl distearate Q-182S or Decaglyceryl monolaurate Q-12S manufactured by Taiyo Kagaku Co., Ltd.), sorbitan fatty acid ester (e.g., NIKKOLSL-10 manufactured by Nikko Chemicals Co., Ltd.), sugar ester (e.g., DK Ester F-110 manufactured by DKS Co. Ltd.), polysorbate (Emazole S-120 series manufactured by Kao Corporation), and the like.

(Printing Method)

The printing method using the inkjet ink of the present embodiment is not particularly limited. Printing using an inkjet device, such as a commercially available inkjet printer, may be used. Therefore, the inkjet ink of the present embodiment has a wide application range and is very useful. For example, the inkjet ink of the present embodiment can be printed using a drop-on-demand inkjet device including a piezoelectric element (piezoelectric ceramic) as an actuator, or an inkjet device of other type.

Examples of the drop-on-demand inkjet device include a thermal-inkjet type device ejecting an inkjet ink using water vapor pressure which is generated by instantaneously heating a micro-heating element to a high temperature (of 200° ° C. to 300° C.), an electrostatic-type device ejecting an inkjet ink by electrostatically vibrating an actuator, an ultrasonic-type device using an ultrasonic cavitation phenomenon, and other devices. If the inkjet ink of the present embodiment has charging performance, a continuous injection device may be used.

[Tablet]

The inkjet ink of the present embodiment may be used for printing characters or an image on the surfaces of tablets, for example, using the above methods. The following description explains a configuration of a tablet having an image printed by the inkjet ink of the present embodiment.

The tablet of the present embodiment is, for example, a pharmaceutical tablet. Examples of the pharmaceutical tablet herein include film-coated tablets having an outermost surface on which a water-soluble surface layer is formed, as well as uncoated tablets (bare tablets), sugar-coated tablets, enteric tablets, and orally disintegrating tablets.

Figure 1:
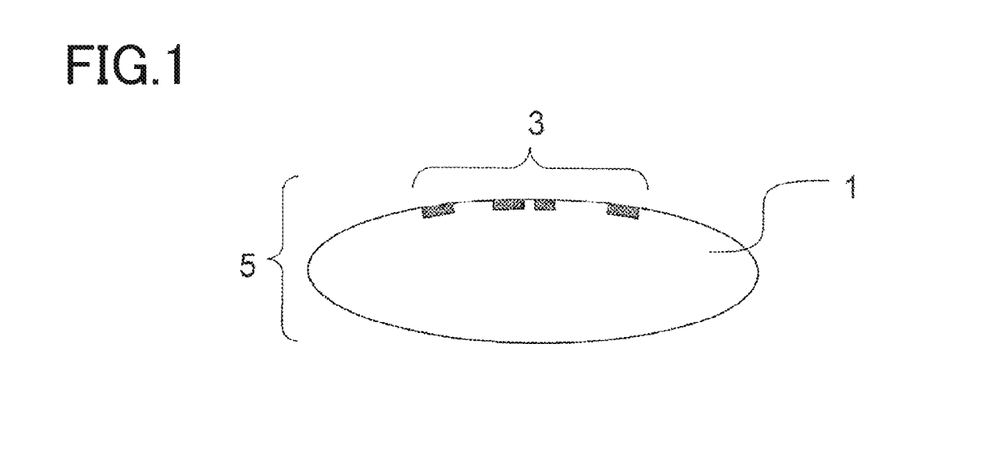
FIG. 1 is a schematic cross-sectional view illustrating an example of a tablet (uncoated tablet) according to an embodiment of the present invention.

FIG. 1 is a schematic cross-sectional view illustrating an example of a pharmaceutical tablet (uncoated tablet) having a print pattern (characters or image) FIG. 1 shows a cross section of an uncoated tablet 5 in which a printed image 3 such as of characters is printed on top face of a tablet body 1.

Figure 2:
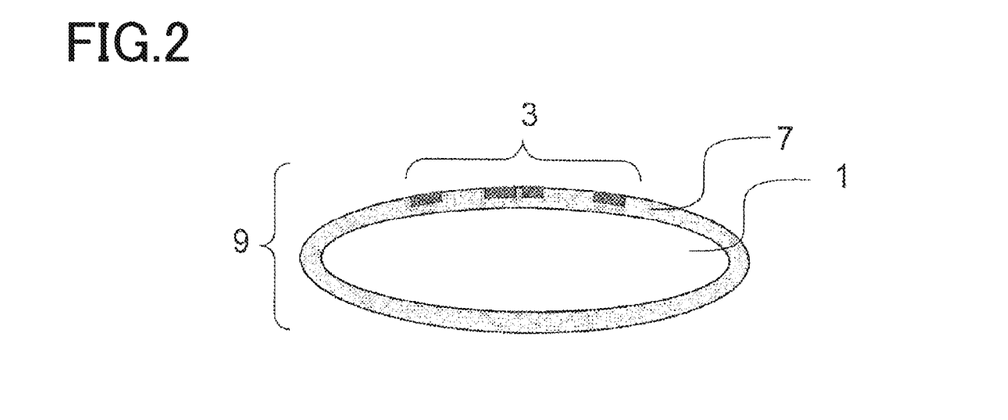
FIG. 2 is a schematic cross-sectional view illustrating an example of a tablet (film-coated tablet) according to an embodiment of the present invention.

FIG. 2 is a schematic cross-sectional view illustrating an example of a pharmaceutical tablet (film-coated tablet) having a print pattern (characters or image) FIG. 2 shows a cross section of a film-coated tablet 9 in which a printed image 3 such as of characters is printed on top face of a tablet body 1 covered with a film coating layer 7.

Figure 3:
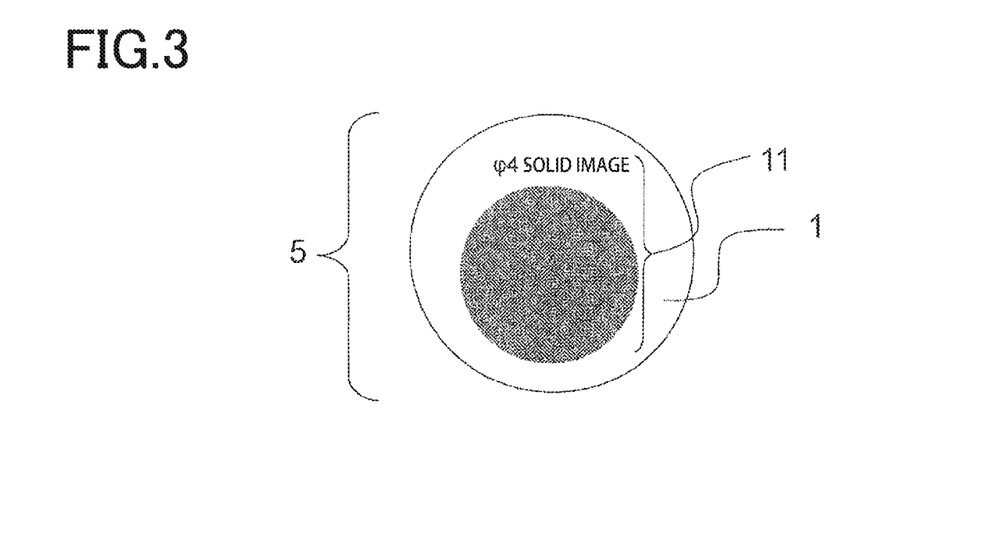
FIG. 3 is a diagram illustrating an example of a printed image for a tablet (uncoated tablet) according to an embodiment of the present invention.
Figure 4:
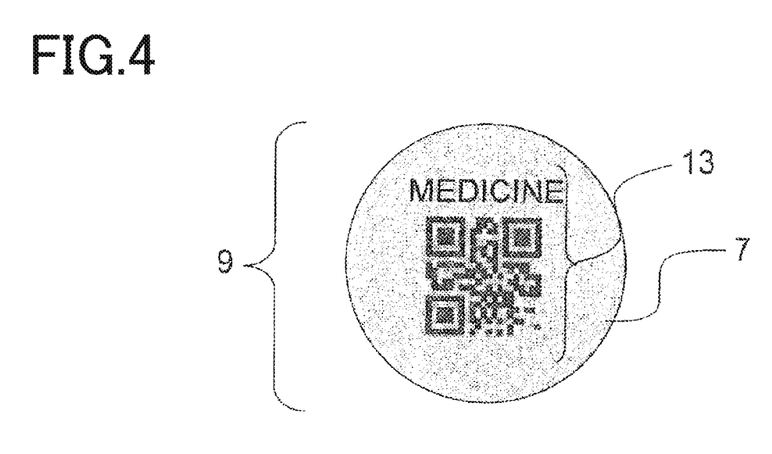
FIG. 4 is a diagram illustrating an example of a printed image for a tablet (film-coated tablet) according to an embodiment of the present invention.

As shown in FIG. 3, in the present embodiment, a solid image may be printed on an uncoated tablet as a printed image 11, or as shown in FIG. 4, a QR barcode may be printed on a film-coated tablet as a printed image 13.

The pharmaceutical table may contain unlimited active ingredients. For example, the active ingredients include, but are not limited to, substances effective for preventing or treating various diseases (e.g., substances having sleep-inducing effect, tranquilizer activity, antibacterial activity, antihypertensive effect, anti-angina activity, analgesic effect, anti-inflammatory activity, tranquilizing effect, diabetes treatment activity, diuretic effect, anticholinergic activity, anti-hyperacidity effect, antiepileptic effect, ACE inhibitory activity, ß-receptor antagonist or agonist activity, anesthetic action, appetite suppression effect, antiarrhythmic effect, antidepressant effect, anticoagulant activity, antidiarrheal effect, antihistamine activity, antimalarial effect, antitumor activity, immunosuppressive activity, antiparkinsonian effect, antipsychotic effect, antiplatelet activity, antihyperlipidemic effect, and the like), substances having scavenging effect, perfume, and substances having deodorant action.

In the tablet of the present embodiment, carriers which are tolerated from the perspectives of usage with the active ingredients may be mixed as necessary. For example, pharmaceutical tablets may comprise carriers which are tolerated from pharmaceutical perspectives. As carriers tolerated from pharmaceutical perspectives, various organic or inorganic carriers may be mixed, which are commonly used as pharmaceutical materials, such as an excipient, lubricant, binder, disintegrant or thickener. As necessary, additives, such as an antiseptic, antioxidant, colorant or sweetener, may be used.

Although the present embodiment has been described taking an example of a pharmaceutical tablet as a tablet, tablet is not limited to this tablet of the present invention. An object to be printed for the inkjet ink of the present embodiment is not particularly limited. For example, the inkjet ink of the present embodiment may be printed on the surfaces of various tablets, including tablets to be administered to non-human animals (e.g., pets, livestock, poultry, etc.), or tablets of feed, fertilizers, cleaning agents, and food such as soda-pop flavored confectionery. The inkjet ink of the present embodiment does not particularly limit the size of an object to be printed, but may be applied to tablets of various sizes.

(Advantageous Effects of the Present Embodiment)

(1) The inkjet ink of the present embodiment, which is edible, comprises a food color containing at least sodium copper chlorophyllin and a pigment other than sodium copper chlorophyllin, and a dispersion medium containing propylene glycol, and has a propylene glycol content in the range of 0.001 mass % or more and 19 mass % or less relative to the total mass of the inkjet ink.

With this composition, even after long-term storage of the inkjet ink in which a food color containing at least sodium copper chlorophyllin and a pigment other than sodium copper chlorophyllin is dispersed in a dispersion medium containing propylene glycol, the occurrence of precipitation due to the pigment components or other components can be prevented, or printing can be easily resumed, compared to the conventional art.

(2) The inkjet ink of the present embodiment may have a propylene glycol content in the range of 0.01 mass % or more and 2.5 mass % or less relative to the total mass of the inkjet ink.

With this composition, the occurrence of precipitation due to the pigment components or other components can be reliably prevented, and printing can be reliably and easily resumed, compared to the conventional art.

(3) The inkjet ink of the present embodiment may have a food color content in the range of 1 mass % or more and 10 mass % or less relative to the total mass of the inkjet ink.

With this composition, the occurrence of precipitation due to the pigment components or other components can be further prevented, and printing can be even more easily resumed, compared to the conventional art.

(4) The pigment other than sodium copper chlorophyllin contained in the inkjet ink of the present embodiment may be at least one of New Coccine, erythrosine and Brilliant Blue FCF.

With this composition, the occurrence of precipitation due to the pigment components or other components can be further prevented, and printing can be even more easily resumed, compared to the conventional art. With this composition, the inkjet ink can have a gray hue. Inks presenting a gray hue have a wide range of use and high versatility.

(5) The food color in the inkjet ink of the present embodiment may have a content of a pigment other than sodium copper chlorophyllin in the range of 0.1 parts by mass or more and 1.5 parts by mass or less relative to 1 part by mass of sodium copper chlorophyllin.

With this composition, the occurrence of precipitation due to the pigment components or other components can be further prevented, and printing can be even more easily resumed, compared to the conventional art.

(6) The inkjet ink of the present embodiment may further comprise glycerin as a dispersion medium, and the propylene glycol content may be less than the glycerin content.

With this composition, drying speed at the nozzle of the inkjet head during printing may be reduced and easy resumption of printing is better ensured.

(7) The inkjet ink of the present embodiment may be directly printed on the surfaces of tablets or food, or may be used for packages directly contacting pharmaceutical products or food.

With this composition, the inkjet ink can be directly printed on the surfaces of tablets or food, or can be used for packages directly contacting pharmaceutical products or food.

(8) The tablet of the present embodiment is provided with a printed image 3 which has been printed using the inkjet ink described above.

With this configuration, the printed image portion on the surface of the tablet can be imparted with edibility.

(9) The tablet of the present embodiment may be a pharmaceutical tablet.

With this configuration, the printed image portion on the surface of the pharmaceutical tablet can be imparted with edibility.

Examples

The present invention will be further described in detail by way of examples; however the present invention is not limited to these examples.
(Production of Inkjet Ink)

A procedure of preparing an inkjet ink will be described.

An inkjet ink contains such components as pigments, an organic solvent, water, an internal-sizing resin and a leveling agent. In the procedure of preparing an inkjet ink, water was firstly mixed with an organic solvent to obtain a mixed solvent. Next, an internal-sizing resin and a leveling agent were added to the mixed solvent to obtain clear base liquid. Finally, a color material was added to the clear base liquid. Respective inks of the present examples were prepared in this way. Each component will be specifically described below.

As water composing the ink, purified water (ion-exchanged water) was used.

As the organic solvent, glycerin and propylene glycol were used.

The internal-sizing resin is a material serving as a non-volatile resin component in the ink. In each of the present examples, hydroxypropylcellulose (HPC-SSL manufactured by Nippon Soda Co., Ltd.) was used as an internal-sizing resin.

As the leveling agent, decaglyceryl monostearate (Q-18S manufactured by Taiyo Kagaku Co., Ltd.), which was a type of glycerin fatty acid ester, was used. The leveling agent is a material controlling the surface tension of the ink droplets ejected from the inkjet head so that the droplets are formed with a good shape. The surface tension of the ink droplets is preferred to be in the range of 24 mN/m to 34 mN/m. However, from the perspective of wettability on the surface layer of a tablet or permeability inside thereof, the surface tension is required to be determined so as to have as small a value as possible, i.e., a value imparting good wettability. In this regard, in the present examples, the inks were each controlled so that the droplets would have a surface tension in the range of 24 mN/m to 28 mN/m. A smaller surface tension does not always bring about good results. For example, a surface tension of less than 24 mN/m does not necessarily form droplets but may cause an ejection failure, such as a mist formation failure or occurrence of a splash phenomenon (breakage of ejected droplets).

In each of the present examples, the above components were stirred and mixed to prepare a clear base liquid. After that, various pigments were mixed to obtain inkjet inks of Examples 1 to 15 and Comparative Examples 1 to 3. Table 1 shows compositions of the inkjet inks obtained in this way. In Table 1, the mark "-" indicates that the material is not used.

TABLE 1

|  |  | Examples | | | | | | |
|---|---|---|---|---|---|---|---|---|
|  |  | 1 | 2 | 3 | 4 | 5 | 6 | 7 |
| Color material | Total color material (mass %) | (7.0%) | (1.0%) | (7.0%) | (7.0%) | (7.0%) | (10.0%) | (7.0%) |
|  | Sodium copper chlorophyllin (mass %) | 6% | 0.50% | 6% | 6% | 3.50% | 3.50% | 3.50% |
|  | Food Red No. 102 (mass %) | — | — | — | — | 3.50% | 6.50% | 3.50% |
|  | Food Blue No. 1 (mass %) | 1% | 0.50% | 1% | — | — | — | — |
|  | Food Red No. 3 (mass %) | — | — | — | 1% | — | — | — |
|  | Food Yellow No. 4 (mass %) | — | — | — | — | — | — | — |
| Purified water (mass %) |  | 71.599% | 76.10% | 70.10% | 70.10% | 70.10% | 67.10% | 52.60% |
| Organic solvent | Glycerin (mass %) | 20% | 20% | 20% | 20% | 20% | 20% | 20% |
|  | Propylene glycol (mass %) | 0.001% | 1.50% | 1.50% | 1.50% | 1.50% | 1.50% | 19.00% |

TABLE 1-continued

|  |  | | | | | | | |
|---|---|---|---|---|---|---|---|---|
| Leveling agent | Decaglyceryl monostearate (mass %) | 0.20% | 0.20% | 0.20% | 0.20% | 0.20% | 0.20% | 0.20% |
| Internal-sizing resin | Hydroxypropyl-cellulose (mass %) | 1.20% | 1.20% | 1.20% | 1.20% | 1.20% | 1.20% | 1.20% |
| Total mass |  | 100.00% | 100.00% | 100.00% | 100.00% | 100.00% | 100.00% | 100.00% |
| Evaluation | Precipitation (filtering) | Not precipitated | Not precipitated | Not precipitated | Not precipitated | Not precipitated | Not precipitated | Not precipitated |
|  | Inkjet printing stability | Fair | Fair | Excellent | Excellent | Excellent | Fair | Fair |

|  |  |  | Examples | | | | | |
|---|---|---|---|---|---|---|---|---|
|  |  |  | 8 | 9 | 10 | 11 | 12 | 13 |
| Color material | Total color material (mass %) |  | (7.0%) | (6.6%) | (7.0%) | (7.0%) | (7.0%) | (7.0%) |
|  | Sodium copper chlorophyllin (mass %) |  | 3.20% | 6.00% | 3.20% | 3.20% | 2.80% | 3.20% |
|  | Food Red No. 102 (mass %) |  | 2.80% | 0.30% | 2.80% | 2.80% | 3.00% | 2.80% |
|  | Food Blue No. 1 (mass %) |  | 1.00% | 0.30% | 1.00% | 1.00% | 1.20% | 1.00% |
|  | Food Red No. 3 (mass %) |  | — | — | — | — | — | — |
|  | Food Yellow No. 4 (mass %) |  | — | — | — | — | — | — |
| Purified water (mass %) |  |  | 70.10% | 70.50% | 69.10% | 71.59% | 70.10% | 90.10% |
| Organic solvent | Glycerin (mass %) |  | 20% | 20% | 20% | 20% | 20% | — |
|  | Propylene glycol (mass %) |  | 1.50% | 1.50% | 2.50% | 0.01% | 1.50% | 1.50% |
| Leveling agent | Decaglyceryl monostearate (mass %) |  | 0.20% | 0.20% | 0.20% | 0.20% | 0.20% | 0.20% |
| Internal-sizing resin | Hydroxypropyl-cellulose (mass %) |  | 1.20% | 1.20% | 1.20% | 1.20% | 1.20% | 1.20% |
| Total mass |  |  | 100.00% | 100.00% | 100.00% | 100.00% | 100.00% | 100.00% |
| Evaluation | Precipitation (filtering) |  | Not precipitated | Not precipitated | Not precipitated | Not precipitated | Not precipitated | Not precipitated |
|  | Inkjet printing stability |  | Excellent | Good | Good | Good | Good | Good |

|  |  |  | Examples | | Comparative Examples | | |
|---|---|---|---|---|---|---|---|
|  |  |  | 14 | 15 | 1 | 2 | 3 |
|  | Color material | Total color material (mass %) | (7.0%) | (7.0%) | (7.0%) | (7.0%) | (7.0%) |
|  |  | Sodium copper chlorophyllin (mass %) | 2.20% | 5.00% | 3.20% | 6% | 6% |
|  |  | Food Red No. 102 (mass %) | 2.80% | — | 2.80% | — | — |
|  |  | Food Blue No. 1 (mass %) | 1.00% | — | 1.00% | 1% | — |
|  |  | Food Red No. 3 (mass %) | — | — | — | — | 1% |
|  |  | Food Yellow No. 4 (mass %) | 1.00% | 2.00% | — | — | — |
|  | Purified water (mass %) |  | 70.10% | 70.10% | 70.10% | 70.10% | 70.10% |
|  | Organic solvent | Glycerin (mass %) | 20% | 20% | 2% | 2% | 2% |
|  |  | Propylene glycol (mass %) | 1.50% | 1.50% | 20.00% | 20.00% | 20.00% |

TABLE 1-continued

| | | | | | | |
|---|---|---|---|---|---|---|
| Leveling agent | Decaglyceryl monostearate (mass %) | 0.20% | 0.20% | 0.20% | 0.20% | 0.20% |
| Internal-sizing resin | Hydroxypropyl-cellulose (mass %) | 1.20% | 1.20% | 1.20% | 1.20% | 1.20% |
| Total mass | | 100.00% | 100.00% | 100.00% | 100.00% | 100.00% |
| Evaluation | Precipitation (filtering) | Not precipitated | Not precipitated | Precipitated | Precipitated | Precipitated |
| | Inkjet printing stability | Good | Good | Poor | Poor | Poor |

(Filtering)

The above inks were stored in a dark place at a temperature of 20° and a relative humidity of 65% for 3 months. After that, the inks were each passed through a membrane filter to detect the occurrence of precipitation, based on whether the ink could pass through the filter without stopping halfway. Specifically, 200 g of each of the inks was permeated (passed) once through a membrane filter (cellulose acetate membrane filter) having a diameter of 0.8 μm (Minisart 0.8 μm, syringe filter manufactured by Sartorius AG) to detect the occurrence of precipitation. Those inks which passed through the respective membrane filters without stopping halfway were determined as not having suffered precipitation and evaluated as "not precipitated". Those inks which did not pass through the respective membrane filters were determined as having suffered precipitation and evaluated as "precipitated".

(Printing Stability)

A drop-on-demand inkjet head driven by piezoelectric ceramic was used as an inkjet head, which had a print resolution of 600 dpi in a main scanning direction and 600 dpi in a sub-scanning direction (conveyance direction of a recording medium, such as a tablet) and had 2,656 nozzles in total. Using this inkjet head, a test pattern was continuously printed using each ink for 30 minutes at a rate of 6 pl per drop, and after the lapse of 30 minutes, it was confirmed whether the ink had been ejected from all the nozzles without causing ejection failure.

Referring to FIGS. 5(a), 5(b), 5(c), 5(d), 5(e), and 5(f), evaluation criteria for printing stability in the present examples will be described.

Figure 5A:
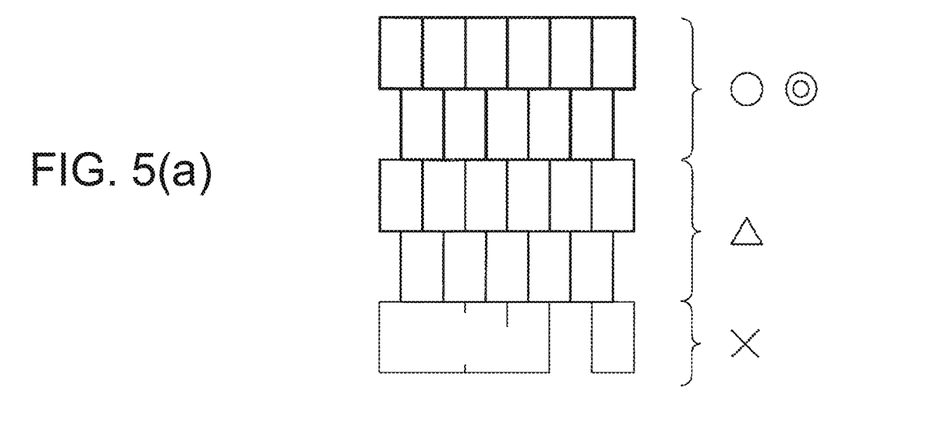
FIGS. 5(a), 5(b), 5(c), 5(d), 5(e), and 5(f) are a set of diagrams illustrating evaluation criteria for printing stability in examples of the present invention.
Figure 5B:
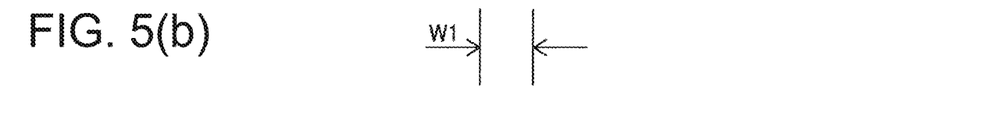
Figure 5C:
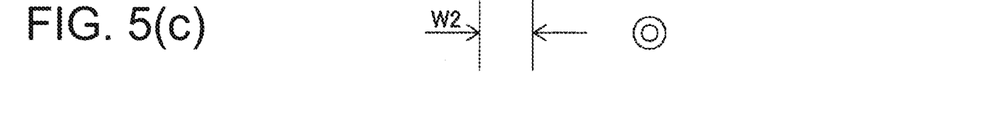
Figure 5D:
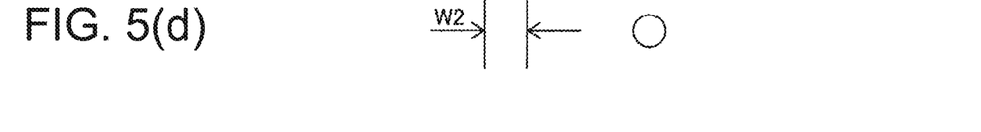
Figure 5E:
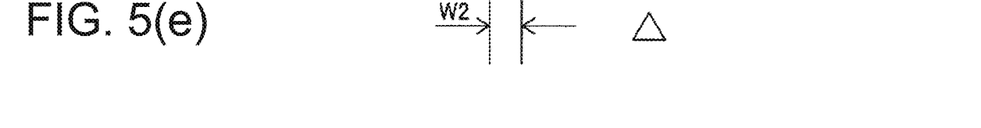
Figure 5F:
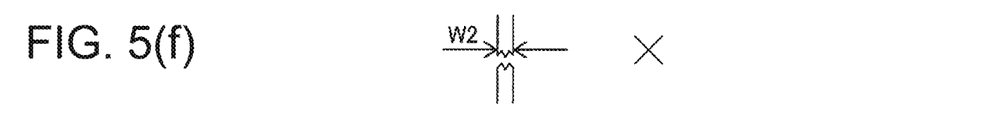

FIGS. 5(a), 5(b), 5(c), 5(d), 5(e), and 5(f) are a set of diagrams illustrating evaluation criteria for printing stability in the present examples. FIG. 5(a) shows a test pattern used for evaluating printing stability in the present examples. This test pattern is configured by straight lines extending in the horizontal direction of FIG. 5(a) and straight lines extending in the vertical direction of FIG. 5(a), and each straight line has a width of 0.5 mm. FIG. 5(b) shows a line width w1 immediately after the start of printing of the test pattern. FIGS. 5(c) to 5(f) each show a line width w2 immediately after the lapse of 30-minute continuous printing of the test pattern. In the present examples, ink was evaluated to be "Excellent", as shown in FIG. 5(c), if the line width w2 immediately after the lapse of 30-minute continuous printing of the test pattern was not decreased compared to the line width w1 immediately after the start of printing of the test pattern, i.e., if the decrease ratio of the line width was substantially 0%. In the present examples, ink was evaluated to be "Good", as shown in FIG. 5(d), if the line width w2 immediately after the lapse of 30-minute continuous printing of the test pattern was decreased compared to the line width w1 immediately after the start of printing of the test pattern, i.e., if the decrease ratio of the line width was 10% or less. In the present examples, ink was evaluated to be "Fair", as shown in FIG. 5(e), if the line width w2 immediately after the lapse of 30-minute continuous printing of the test pattern was decreased compared to the line width w1 immediately after the start of printing of the test pattern, i.e., if the decrease ratio of the line width exceeded 10%, but the print lines configuring the test pattern had no line breakages (no disconnected portions or unprinted portions). In the present examples, ink was evaluated to be "Poor", as shown in FIG. 5(f), if there were line breakages (unprinted portions) in the print lines immediately after the lapse of 30-minute continuous printing of the test pattern.

The evaluation criteria for printing stability in the present examples are summarized as follows.

Excellent: Ejection failure was confirmed at none of the nozzles. In addition, no decrease of line width was visually confirmed in the test pattern.

Good: Ejection failure was confirmed at none of the nozzles, but decrease of line width (10% or less) was visually confirmed.

Fair: Ejection failure was confirmed at none of the nozzles, but decrease of ejection was confirmed in part of the nozzles. Accordingly, decrease of line width (exceeding 10%) was visually confirmed in the test pattern. However, no line breakages (unprinted portions) were confirmed in the test pattern.

Poor: Ejection failure was confirmed in part of the nozzles. Accordingly, line breakages (unprinted portions) were confirmed in the test pattern.

As long as the evaluation of the printing stability is Excellent, Good or Fair, the ink has high quality. Even if the printing stability is evaluated as being Poor, the ink has no problem in quality (medicinal effect or the like), although visibility remains a problem.

As can be seen from the above results, as long as an inkjet ink, which comprises a food color containing at least sodium copper chlorophyllin and a pigment other than sodium copper chlorophyllin, and a dispersion medium containing propylene glycol, has a propylene glycol content in the range of 0.001 mass % or more and 19 mass % or less relative to the total mass of the inkjet ink, the occurrence of precipitation of the pigment components or other components are prevented, and deterioration in printing stability (printing resumability) is prevented, even if the inkjet ink is stored for a long period of time.

[Reference Signs List] 1: Tablet; 3: Printed image; 5: Uncoated tablet; 7: Film coating layer; 9: Film-coated tablet; 11: Printed image (solid image) on uncoated tablet; 13: Printed image (QR code) on film-coated tablet

What is claimed is:

1. An inkjet ink that is edible, comprising:
a food color comprising at least sodium copper chlorophyllin and a second pigment other than the sodium copper chlorophyllin; and,
a dispersion medium consisting of propylene glycol, glycerin and water,
wherein a content of the propylene glycol is in a range of 0.001 mass % or more and 19 mass % or less relative to a total mass of the inkjet ink, the content of the propylene glycol is less than a content of the glycerin.

2. The inkjet ink of claim 1, wherein the content of the propylene glycol is in a range of 0.01 mass % or more and 2.5 mass % or less relative to a total mass of the inkjet ink.

3. The inkjet ink of claim 1, wherein a content of the food color is in a range of 1 mass % or more and 10 mass % or less relative to a total mass of the inkjet ink.

4. The inkjet ink of claim 1, wherein the second pigment is at least one of New Coccine, erythrosine and Brilliant Blue FCF.

5. The inkjet ink of claim 1, wherein a content of the second pigment in the food color is in a range of 0.1 parts by mass or more and 1.5 parts by mass or less relative to 1 part by mass of the sodium copper chlorophyllin.

6. A tablet including a print pattern printed using the inkjet ink of claim 1.

7. The tablet of claim 6, wherein the tablet is a pharmaceutical tablet.

* * * * *